US005674729A

United States Patent [19]

Wimmer et al.

[11] Patent Number: 5,674,729

[45] Date of Patent: Oct. 7, 1997

[54] DE NOVO CELL-FREE SYNTHESIS OF PICORNAVIRUS

[75] Inventors: Eckard Wimmer, Stony Brook; Akhteruzzaman Molla, Port Jefferson; Aniko V. Paul, Setauket, all of N.Y.

[73] Assignee: Research Foundation of State University of New York, Albany, N.Y.

[21] Appl. No.: 268,679

[22] Filed: Jun. 30, 1994

Related U.S. Application Data

[63] Continuation of Ser. No. 846,914, Mar. 6, 1992, abandoned, which is a continuation-in-part of Ser. No. 719,761, Jun. 24, 1991, abandoned.

[51] Int. Cl.$^6$ .......... C12N 7/00

[52] U.S. Cl. .......... 435/235.1

[58] Field of Search .......... 435/69.1, 70.1, 435/183, 239, 240.2, 235.1

[56] References Cited

U.S. PATENT DOCUMENTS 4,403,035 9/1983 Anderson et al. .......... 435/172.3

OTHER PUBLICATIONS

Garoff et al, Journal of Molecular Biology (1978), pp. 587–600.

Fernandez–Thomas et al., *J. Virology,* 12(5): 1122–1130 (1973).

Fernandez–Tomas et al., *J. Virology,* 12(5):1181–1183 (1973).

Brown et al., *Virology,* 97:396–405 (1979).

Rancaniello et al., *Science,* 214: 914–918 (1981).

Palmenberg, *J. Virology,* 44(3): 900–906 (1982).

Van der Werf, et al., *Proc. Natl. Acad. Sci U.S.A.,* 83: 2330–2334 (1986).

Dorner, et al., *J. Virol.,* 50(2):507–514 (1984).

Grubman, et al., *J. Virol.,* 56: 120–126 (1985).

Ypma–Wong et al., *Nucleic Acids Res.,* 15(5):2069–2088 (1987).

Rose et al., *PNAS USA,* 75(6):2732–2736 (1976).

Villa–Komaroff et al., *PNAS USA,* 72(10):4157–4161 (1975).

Shih et al., *PNAS USA,* 75(12): 5807–5811 (1978).

Ayoama et al., *Proc. Natl. Acad. Sci. USA,* 78(12):7285–7289. (1981).

B.N. Fields, D.M. Knipe et al., ed., *Virology,* 2d Ed. Raven Press Ltd. New York 1990 Chapters 1, 20. pp. 3–7, 507–548.

H.R.B. Pelham and R.J. Jackson, *Eur. J. Biochem.,* 67:247–256 (1976).

J.P. Putnak et al., *Microbiol. Rev.,* 45:287–315 (1981).

A.L. Bak, Current Top, *Microbiol. Immunol.,* 61:89–149 (1973).

*Primary Examiner*—Mindy Fleisher
*Assistant Examiner*—Terry A. McKelvey
*Attorney, Agent, or Firm*—Morgan & Finnegan, L.L.P.

[57] ABSTRACT

A process for the de novo synthesis of a picornavirus using a cell-free medium has been developed. The cell-free medium is prepared from a lysate of mammalian cells from which the nuclei and mitochondria has been removed, endogenous mRNA deactivated and supplemented with nucleoside triphosphates, tRNA, amino acids and precursors necessary for generating proteins. The genomic RNA of the picornavirus or rhinovirus is added to the cell-free medium and after incubation at about 30° C. to 40° C. of from about 4 to 24 hours infectious, mature virus particles are formed.

18 Claims, 4 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 22
( B ) TYPE: NUCLEIC ACID
( C ) STRANDEDNESS: SINGLE
( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: NO ( v i ) ORIGINAL SOURCE:
( A ) ORGANISM: POLIOVIRUS
( B ) STRAIN: PVI(M)

( v i i i ) POSITION IN GENOME:
( A ) CHROMOSOME/SEGMENT:
( B ) MAP POSITION: 3280-3301,

-continued ( x i ) SEQUENCE DESCRIPTION: SEQ ID NO:1:

AGTCTGGTGC CCGCGTCCAC CG 22

( 2 ) INFORMATION FOR SEQ ID NO:2:

( i ) SEQUENCE CHARACTERISTICS:
( A ) LENGTH: 24
( B ) TYPE: NUCLEIC ACID
( C ) STRANDEDNESS: SINGLE
( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: YES ( v i ) ORIGINAL SOURCE:
( A ) ORGANISM: POLIOVIRUS
( B ) STRAIN: PVI(M)

( v i i i ) POSITION IN GENOME:
( A ) CHROMOSOME/SEGMENT:
( B ) MAP POSITION: 3983-4007

( x i ) SEQUENCE DESCRIPTION: SEQ ID NO:2:

CGTTGATGGT GAACCGGTGA GTCC 24

( 2 ) INFORMATION FOR SEQ ID NO:3:

( i ) SEQUENCE CHARACTERISTICS:
( A ) LENGTH: 6
( B ) TYPE: NUCLEIC ACID
( C ) STRANDEDNESS: SINGLE
( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: YES ( v i ) ORIGINAL SOURCE: N.A.

( v i i i ) POSITION IN GENOME: N.A.

( x i ) SEQUENCE DESCRIPTION: SEQ ID NO:3:

AGGCCT 6

( 2 ) INFORMATION FOR SEQ ID NO:4:

( i ) SEQUENCE CHARACTERISTICS:
( A ) LENGTH: 12
( B ) TYPE: NUCLEIC ACID
( C ) STRANDEDNESS: SINGLE
( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: YES ( v i ) ORIGINAL SOURCE: N.A.

( v i i i ) POSITION IN GENOME: N.A.

( x i ) SEQUENCE DESCRIPTION: SEQ ID NO:4:

AGGCCTGGAT CC 12

( 2 ) INFORMATION FOR SEQ ID NO:5:

( i ) SEQUENCE CHARACTERISTICS:
( A ) LENGTH: 11
( B ) TYPE: NUCLEIC ACID
( C ) STRANDEDNESS: SINGLE
( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: YES ( v i ) ORIGINAL SOURCE: N.A.

( v i i i ) POSITION IN GENOME: N.A.

( x i ) SEQUENCE DESCRIPTION: SEQ ID NO:5:

GCCNNNNNGC C 11

( 2 ) INFORMATION FOR SEQ ID NO:6:

( i ) SEQUENCE CHARACTERISTICS:
( A ) LENGTH: 41
( B ) TYPE: NUCLEIC ACID
( C ) STRANDEDNESS: SINGLE
( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: YES ( v i ) ORIGINAL SOURCE: N.A.

( v i i i ) POSITION IN GENOME: N.A.

( x i ) SEQUENCE DESCRIPTION: SEQ ID NO:6:

GATCCCGCGA AATTAATACG ACTCACTATA GGTTAAAACA G 41

( 2 ) INFORMATION FOR SEQ ID NO:7:

( i ) SEQUENCE CHARACTERISTICS:
( A ) LENGTH: 3
( B ) TYPE: NUCLEIC ACID
( C ) STRANDEDNESS: SINGLE
( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: YES ( v i ) ORIGINAL SOURCE: N.A.

( v i i i ) POSITION IN GENOME: N.A.

( x i ) SEQUENCE DESCRIPTION: SEQ ID NO:7:

AGG 3

( 2 ) INFORMATION FOR SEQ ID NO:8:

( i ) SEQUENCE CHARACTERISTICS:
( A ) LENGTH: 2
( B ) TYPE: NUCLEIC ACID
( C ) STRANDEDNESS: SINGLE

-continued ( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: YES ( v i ) ORIGINAL SOURCE: N.A.

( v i i i ) POSITION IN GENOME: N.A.

( x i ) SEQUENCE DESCRIPTION: SEQ ID NO:8:

GG 2

DE NOVO CELL-FREE SYNTHESIS OF PICORNAVIRUS

CROSS REFERENCE TO RELATED APPLICATIONS

This is a continuation of application Ser. No. 07/846,914, filed on Mar. 6, 1992 abandoned, which is a continuation-in-part application of application Ser. No. 07/719,761 filed Jun. 24, 1991, which is now abandoned.

The invention was made with Government support under No. AI15122-17 awarded by National Institute of Health. The Government has certain rights in this invention.

INTRODUCTION

This invention is directed to an in vitro process for the de novo synthesis of infectious picornaviruses and a cell-free medium useful in the process. More particularly, the invention is directed to an in vitro process using a cell-free medium to synthesize mature, infectious picornaviruses de novo. Most particularly, the invention is directed to using a cell-free medium from which the nuclei and mitochondria of the cells have been removed, to synthesize infectious picornavirus and rhinovirus.

BACKGROUND

The Picornaviridae, among the smallest ribonucleic acid-containing viruses known, comprise one of the largest and most important families of human and agricultural pathogens. Poliovirus, human rhinovirus, human hepatitis A virus, encephalomyocarditis virus and food-and-mouth disease virus are all members of the picornavirus family.

Because of the economic and medical importance of picornaviruses, they have been the subject of much study. Studies on the molecular biology of these viruses became possible when it was discovered that poliovirus could be propagated in cultured cells, such as HeLa cells, and other picornaviruses can be propagated in L cells or BHK cells. Crucial advances, such as the development of a plaque assay for infectivity and of methods of purification of viruses, proteins and polypeptides opened the way for structural analysis of these viruses.

The family of picornavirus is currently divided into four genera: enteroviruses, cardioviruses, rhinoviruses and aphthoviruses. The poliovirus, the prototype of picornaviruses, is an enterovirus. The etiologic agents of the common cold are rhinoviruses. The foot-and-mouth disease viruses are aphthoviruses. The encephalomyocartditis virus is a cardiovirus. Present knowledge indicates that revision of this classification is probably necessary. However, for the present purposes, this classification scheme suffices. Members of each genus is then subclassified into serotypes, and then to strains. Morphologically, the members of the four genera are not distinguishable by electronmicroscopy.

Human rhinoviruses (HRVs) consists of a group of at least 115 antigenically distinct serotypes that belong to the family of Picornavirus. A better understanding of the biochemical mechanisms used during viral infection is needed to develop novel approaches to control HRV infections in common cold. Recently, the complete nucleotide sequence of a cDNA, representing the genomic RNA of HRV-14 and other serotypes of rhinoviruses, was determined. Thus far, all attempts have failed to translate the full length HRV RNA in cell free extracts.

All picornaviruses including poliovirus, cardiovirus, human rhinoviruses and aphthoviruses contain four polypeptide chains: VP1, VP2, VP3, and VP4. These chains are elements of protein subunits called mature "protomers". The protomer is defined as the smallest identical subunit of the virus. Traces of a fifth protein, VP0, which is cleaved to VP2 and VP4 are also observed.

The picornaviral genome consists of a single strand of messenger-active RNA which can be extracted out of virions by shaking aqueous suspensions of virus with an equal volume of phenol and chloroform. On phase separation, the proteins dissolve in the phenol-rich phase, while RNA remains in the aqueous phase. The specific infectivity of the naked RNA is about $10^{-6}$ of the virions.

The genomic messenger active RNA consists of a "+" strand which is polyadenylated at the 3' terminus and carries a small protein, VPg, covalently attached to the 5' end. The first picornaviral RNA to be completely sequenced and cloned into DNA was that of a type 1 poliovirus.

The common organizational pattern of picornaviruses may be represented schematically. See FIG. 5. The number of bases in the RNA range from 7,209 to 8,450. The poliovirus does not have a leader (L) protein.

The pattern of protein synthesis of picornaviruses have been studied since the 1970's and the overall features are now fairly clear. The RNA contains a single long open reading frame encoding a long polypeptide chain, which is called a "polyprotein". The polyprotein is cleaved during translation and is not found as such. A cascade of cleavages, carried out by virus-coded proteinases, ultimately generating usually twelve end products in the case of a virus with a leader (L) protein. Proteinase 3C, or its precursor 3CD mediates most of the cleavages except the early cleavages of the nascent polyprotein and the maturation cleavage of VP0 →VP4 +VP2. The maturation cleavage occurs only after the RNA has been packaged in the protein shell. Without the maturation cleavage, infectivity is not observed.

Picornaviral morphogenesis can formally be described as a tandem three or four stage process in which monomers are converted to a pentamer. 5 pentamers are then assembled into a provirion consisting of the RNA genome within an unstable immature capsid. The final step during which mature virus is formed involved cleavage of most, if not all, of the VP0 chains in the 60 subunit icosahedral capsid.

Viruses are replicating microorganisms that are among the smallest of all life forms. Because of their simplicity, up to the present it is believed that intracellular growth with total dependence on host-cell structural and metabolic components is required (1). Much of the earlier studies of viral propagation and synthesis were conducted using cells susceptible to infection by the virus. In vitro assembly of infectious viruses has been described previously with plant viruses and bacteriophages. In these cases, the components for assembly were either isolated from purified virus particles or from infected cells.

Cell-free assembly of virions has not been possible with picornaviruses possibly because this process may require the proteolytic cleavage of the capsid precursor VP0 possibly as a source of energy. This "maturation cleavage" of VP0 has not been achieved in vitro and its mechanism remains an enigma.

In early 1970's, Fernandez-Tomas and Baltimore (2) reported the isolation of a provirion of poliovirus from infected HeLa cells. The provirion sediments at about 125S and contains three procapsid proteins VP0, VP1 and VP3 and the viral RNA which sediments at about 35S. The sedimentation studies were conducted using detergent treated cytoplasmic extracts through a sucrose gradient.

Fernandez-Tomas et al. (3) also described an attempt to synthesize the poliovirus by incubating cell-free extract that was preinfected with poliovirus. The study was conducted using a cytoplasmic extract of poliovirus infected HeLa cells labelled with $^3$H-leucine and $^{14}$C-uridine. After incubation for 30 minutes at 37° C., an increase of both leucine and uridine labelling in the poliovirus region and structures which sedimented slower than 100S were observed. This is in contrast to the virions which sediment at 155S and the provirions which sediment at 125S.

In 1976, it was found by Pelham and Jackson (4) that endogenous RNA inhibited the translation of exogenous RNA. The efficiency of rabbit reticulocyte cell-free extracts used for the translation of RNA can be increased by preincubation with $CaCl_2$ and micrococcal nuclease which degrades the endogenous mRNA. The micrococcal nuclease-treated extract, when supplemented with excess ethylene-glycol-bis (2-aminoethylether)-N,N$^1$-tretracetic acid (EGTA), selectively inactivates the micrococcal nuclease. This permits improved efficiency of translation of exogenous mRNA after the cell extract had been supplemented with tRNA, amino acids and ATP generating compounds. The studies were conducted using the mRNA of tobacco mosaic virus (TMV RNA) and cow pea mosaic virus. It was also found that addition of mouse liver t-RNA stimulated the translation of the exogenous mRNA. The results showed that the expression products contained larger proteins previously unobtainable in the untreated rabbit reticulocyte system.

Since that time, many attempts to synthesize the poliovirus proteins in vitro have been made.

Villa-Komaroff et al. (5) described the uses of poliovirus RNA to direct synthesis in preincubated extracts of mock-infected or poliovirus infected HeLa cells. The results showed that in both extracts translation of the polio RNA produced nascent viral proteins which had been partially processed, but no evidence for the formation of the provirus or the mature virus was seen.

Shih et al. (6) attempted the translation of poliovirus RNA in rabbit reticulocyte lysates (RRL) which were micrococcal nuclease pretreated. Shih et al. found that translation was optimal at 60 minutes and leveled off after 3 hrs. of incubation. No infectious virus could be detected even after 6 hrs. of incubation. The results indicate that nascent viral proteins together with cleavage products VP0, VP1 and VP3 were found. However, no VP2 or VP4 were observed. It was postulated that the absence of VP2 and VP4 showed that the conditions of the final assembly of the polio virion are not met by the rabbit reticulocyte lysates he used.

Brown and Ehrenfeld (7) attempted in vitro translation of poliovirus RNA by using RRL to which was added a ribosomal salt wash of HeLa cell extracts. Again, the presence of VP0, VP1 and VP3 and other anomalous proteins were observed after incubation. However, the appearance of anomalous proteins was inhibited by the HeLa ribosomal wash. NO VP2 or VP4 were observed and no evidence of formation of provirion or of mature virion was seen.

Dorner et al. (8) studied the in vitro translation of poliovirus RNA in RRL. In this system, aberrant polypeptides were produced and were explained to be caused by the initiation of translation at internal sites of the viral genome. Addition of a HeLa cell extract to the RRL system did reduce the internal initiation of translation. However, no infectious virions were formed.

Ypma-Wong and Semler (9) described the in vitro transcription of a poliovirus cDNA plasmid construct, PT7-14, and the in vitro translation of the mRNA product in a RRL system supplemented with a poliovirus infected HeLa cell extract. Using this media, they studied the synthesis of the 3C proteinase of the poliovirus. No VP2 or VP4 was observed after incubation for 2 hours.

Attempts to assemble other infectious picornaviruses in vitro were reported.

Palmenberg (10) described the in vitro synthesis of encephalomyocarditis virus protein by translation in a RRL. Viral proteins including capsid proteins capable of assembly into viral capsid intermediate structures were formed. Incubation for 15 hours produced a pentameric association of capsid protomers. Complete virions were not observed.

Grubman et al. (11) described the in vitro assembly of foot-and-mouth disease virus (FMDV) from structural proteins isolated from FMDV infected cells. The cytoplasmic extract of infected cells were analyzed to show the presence of intermediates of morphogenesis. Full length FMDV RNA was added to RRL and translation was carried out in vitro. The results indicated that the structural protein complexes assembled in the lysate. However, the presence of the mature virus 140S was not detected.

Neither Palmenberg or Grubman et al reported formation of infectious viral particles. It was believed that the RRL system lacks components essential for morphogenesis (12).

In vitro synthesis of infectious bacteriophages have also been reported.

Anderson et al., U.S. Pat. No. 4,403,035 (13) describe the in vitro assembly of exogenous DNA with viral DNA and inserting the hybrid DNA into an infectious bacteriophage. This can then be used to infect a bacteria to cause it to express the exogenous DNA to produce the desired protein. This is a method of making a gene vector for cloning and expressing the gene and is an entirely different process.

A. Aoyama et al. (14) also describes the in vitro assembly of an infectious phage from purified viral components but this is not a de novo in vitro synthesis.

In vitro synthesis of infectious viruses is desirable for many reasons. It is preferable to study the morphogenesis of the virus in an in vitro media wherein the virus is not enclosed in membranes of the host cells, and anti-viral agents can be conveniently tested without having to penetrate the cell membrane. In this way, the susceptibility of the virus at its various stages of development to an anti-viral agent can be assessed directly, and improved anti-viral agents developed. As study of the cell-free replication of picornaviruses will reveal novel steps in replication that may become targets of chemotherapy.

The picornaviruses are one of the largest and most important group of human and agricultural pathogens. Therefore, it is important to be able to harvest the naked virus synthesized in vitro to study its morphogenesis to develop effective anti-viral agents.

It is, therefore, an objective of the present invention to develop a process for the de novo synthesis of the picornaviruses in vitro.

It is a further objective to develop a cell-free extract for the in vitro synthesis for the production of novel vaccines against picornaviral diseases.

It is also an objective of the present invention to demonstrate that in vitro synthesis of the infectious virions of the picornaviruses can be achieved.

It is a further objective of the present invention to develop a process for the translation and de novo synthesis of polioviruses and human rhinovirus, and other picornaviruses, in vitro.

List of References

1. B. N. Fields, D. M. Knipe et al., ed. *Virology*, 2d. Ed. Raven Press Ltd. New York 1990. Chapters 1, 20.
2. C. B. Fernandez-Tomas and D. Baltimore, *J. Virol.*, 12(5): 1122–1130 (1973). 3. C. B. Fernandez-Tomas et al., *J. Virol.*, 12(5): 1181–1183 (1973).
4. H. R. B. Pelham and R. J. Jackson, *Eur J. Biochem.*, 67:247–256 (1976).
5. L. Villa-Komaroff et al., *PNAS U.S.A.*, 72(10: 4157–4167 (1975).
6. D. S. Shih et al., *PNAS U.S.A*, 75(12): 5807–5811 (1978).
7. B. A. Brown and E. Ehrenfeld, *Virol.*, 97: 396–405 (1979).
8. A. J. Dorner et al., *J. Virol.*, 50(2): 507–514 (1984).
9. M. F. Ypma-Wong and Semler, *J. Virol.*, 61:3181 (1987).
10. A. C. Palmenberg, *J. Virol.*, 44(3): 900–906 (1982).
11. M. J. Grubman et al., *J. Virol.*, 56:120–126 (1985).
12. J. R. Putnak et al., *Microl. Rev.*, 45:287–(1981).
13. Andersen et al., U.S. Pat. No. 4,403,035, issued Sep. 6, 1983.
14. A. Aoyama et al., *PNAS U.S.A.*, 76(12): 7285–7289 (1981).
15. G. Koch, *Current Top. Microbiol. Immunol.*, 61: 89 (1973).
16. Van der Werf et al., *PNAS U.S.A.*, 83(4):2330–2334 (1986).

SUMMARY OF THE INVENTION

According to the present invention, a de novo process for the in vitro synthesis of a picornavirus, comprises the following steps:

A. Preparing a lysate from mammalian cells selected from the group consisting of kidney cells, epithelial cells, liver cells, cells of the central nervous system, fibroblastic cells, transformed or tumorigenic cell lines thereof including HeLa cells, hepatoma cells and L cells; wherein the nuclei and mitochondria were removed; the endogenous mRNA deactivated with micrococcal nuclease, calcium chloride and EGTA, B. Preparing an in vitro synthesis medium by mixing:
   (i) the lysate,
   (ii) about 1 mM ATP,
   (iii) from about 20 μM to 1000 μM each of GTP, CTP and UTP,
   (iv) about 10 mM creatine phosphate,
   (v) about 24 μg/ml creatine phosphokinase,
   (vi) about 2 mM dithiothreitol,
   (vii) about 24 μg/ml calf liver t-RNA,
   (viii) about 12 μM each of 20 amino acids,
   (ix) about 18 mM Hepes, pH 7.4,
   (x) about 240 μM spermidine,
   (xi) from about 50 mM to 200 mM potassium acetate, and
   (xii) from about 1 mM to 4 mM of $Mg^{++}$, wherein the amounts specified represent the final concentration in the medium;

C. Adding isolated viral RNA from virus or in vitro synthesized viral RNA prepared from cDNA to the in vitro synthesis medium; and D. Incubating from about 2 to 24 hrs. at a temperature from about 30° C. to 40° C.

The present invention further relates to a cell-free media prepared from a lysate extracted from mammalian cells, from which the nuclei and mitochondria were removed, the endogenous mRNA deactivated with micrococcal nuclease, calcium chloride and EGTA; and mixing:

(i) the lysate,
(ii) about 1 mMATP,
(iii) and from about 20 μM to 1000 μM each of GTP, CTP and UTP,
(iv) about 10 mM creatine phosphate,
(v) about 24 μg/ml creatine phosphokinase,
(vi) about 2 mM dithiothreitol,
(vii) about 24 μg/ml calf liver t-RNA,
(viii) about 12 μM each of 20 amino acids,
(ix) about 18 mM Hepes, pH 7.4,
(x) about 240 μM spermidine,
(xi) from about 50 mM to 200 mM potassium acetate, and
(xii) from about 1 mM to 4 mM of $Mg^{++}$, wherein the amounts specified represent the final concentration in the medium.

BRIEF DESCRIPTION OF THE DRAWINGS

FIG. 5 is a schematic representation of the organizational pattern of the picornaviruses. VPg encodes a small protein covalently attached to the 5' end. L is the leader protein which is not found in poliovirus. The viral polyproteins encoded by P1, P2, P3, P1 is translated and processed into nucleocapsid proteins VP1, VP2, VP3, and VP4 which are encoded by 1A, 1B, 1C, 1D herein. 2A, 2B, and 2C encode the cleavage products of P2. 3A, 3B, 3C and 3D encode the cleavage products of P3.

DETAILED DESCRIPTION OF THE INVENTION

Figure 1:
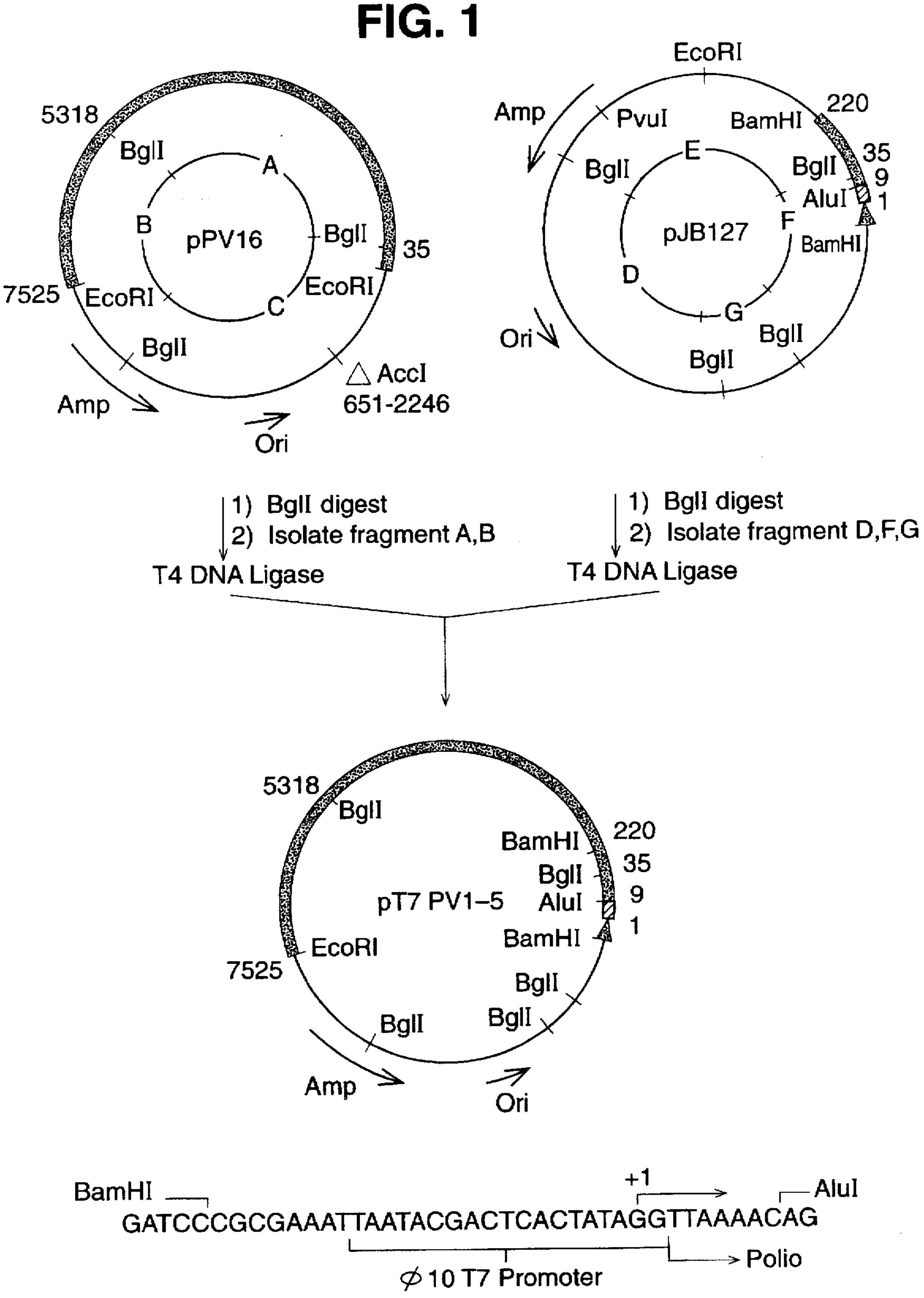
FIG. 1 is a schematic drawing of plasmid pT7 PV1-5 containing poliovirus cDNA and the nucleotide sequence (SEQ ID NO:6) of the T7 promoter.

According to the present invention a process for the de novo, in vitro synthesis of picornaviruses have been developed. The process comprises:

A. Preparing a lysate from mammalian cells selected from the group consisting of kidney cells, epithelial cells, liver cells, cells of the central nervous system, fibroblastic cells, transformed or tumorigenic cell lines thereof, including HeLa cells, hepatoma cells and L cells; from which the nuclei and mitochondria were removed, the endogenous mRNA deactivated with micrococcal nuclease, calcium chloride and EGTA;

B. Preparing an in vitro synthesis medium by mixing:
(i) the lysate,
(ii) about 1 mMATP,
(iii) and from about 20 μM to 1000 μM each of GTP, CTP and UTP,
(iv) about 10 mM creatine phosphate,
(v) about 24 μg/ml creatine phosphokinase,
(vi) about 2 mM dithiothreitol,
(vii) about 24 μg/ml calf liver t-RNA,
(viii) about 12 μM each of 20 amino acids,
(ix) about 18 mM Hepes, pH 7.4,
(x) about 240 μM spermidine,
(xi) from about 50 mM to 200 mM potassium acetate, and
(xii) from about 1 mM to 4 mM of $Mg^{++}$,
wherein the amounts of specified represent the final concentration in the medium;

C. Adding viral RNA from virus or in vitro synthesized viral RNA from cDNA to the in vitro synthesis medium; and D. Incubating from about 2 to 24 hours at a temperature of from about 30° C. to 40° C.

Further, in accordance with the present invention a cell-free extract suitable for the de novo, in vitro synthesis of an infection picornavirus has been developed. The in vitro synthesis medium comprises:

(i) a lysate of mammalian cells selected from the group consisting of kidney cells, epithelial cells, liver cells, cells of the central nervous system, fibroblastic cells, transformed or tumorigenic cell lines thereof including HeLa cells, hepatoma cells and L cells; from which the nuclei and mitochondria were removed, the endogenous mRNA deactivated with micrococcal nuclease, calcium chloride and EGTA;
(ii) about 1 mMATP,
(iii) from about 20 μM to 1000 μM each of GTP, CTP and UTP,
(iv) about 10 mM creatine phosphate,
(v) about 24 μg/ml creatine phosphokinase,
(vi) about 2 mM dithiothreitol,
(vii) about 24 μg/ml calf liver t-RNA,
(viii) about 12 μM each of 20 amino acids,
(ix) about 18 mM Hepes, pH 7.4,
(x) about 240 μM spermidine,
(xi) from about 50 mM to 200 mM potassium acetate, and
(xii) from about 1 mM to 4 mM $Mg^{++}$,
wherein the amounts specified represent the final concentration in the medium.

The cell-free extract is highly efficient for the translation of poliovirus RNA in vitro. Further, by introducing a cycle of freezing at −80° C., thawing to room temperature followed with centrifugation after removal of the nuclei and mitochondria but before deactivation of endogenous mRNA, the efficiency of virus production was found to be increased many folds. Therefore, even though the treatment is not absolutely necessary, it is much preferred.

Mammalian cells suitable for use in preparing the in vitro cell-free extract includes: kidney cells, epithelial cells, liver cells, cells of the central nervous system, transformed or tumorigenic cell lines thereof including HeLa cells, hepatoma cells and L cells. The infectivity of the picornaviruses in the various cell lines are known. In selecting suitable cells, cells of primate origin will be found to be suitable for enteroviruses, rhinoviruses, cardioviruses. Whereas, cell lines from hamsters such as BHK will be found suitable for FMDV.

The nuclei and mitochondria are removed by known methods. For example, cells from a cell line suitable for the synthesis of the desired picornaviruses are harvested by centrifugation, washed with a suitable buffered solution such as PBS, saline and resuspended in N-2-hydroxylethylpiperazine-$N^1$-ethanesulfonic acid (Hepes) pH 7.4 suitably adjusted with KOAc and $Mg(OAc)_2$ and dithiothreitol (DTT). The cells are then swollen and disrupted at 4° C. with a Dounce homogenizer. The nuclei and mitochondria can be removed by centrifugation. The supernatant is dialyzed against a solution containing KOAc, $Mg(OAc)_2$ and DTT. The supernatant is frozen at −80° C., then thawed to room temperature and again centrifuged. The cell-free extract is then made dependent upon mRNA addition by the method of Pelham and Jackson (4), by deactivating the endogenous RNA with micrococcal nuclease and calcium chloride followed by treatment with EGTA. For ease of short-term storage of about one month, the lysate can be adjusted to 10% by volume with glycerol and frozen at −80° C. For longer term storage, the lysate is stored at the temperature of liquid nitrogen.

The in vitro synthesis medium is conveniently prepared in small lots. For example, to make 250 μl of the in vitro synthesis medium 93 μl of the cell-free extract can be used. To this can be added the nucleoside triphosphates, ATP, GTP, CTP and UTP to provide energy and precursors for virus production. The ATP should generally be present at a higher amount. For example, 1 mM of ATP to a mixture of from about 40 μM to 250 μM each of GTP, CTP and UTP is preferred for poliovirus. Other components necessary for the synthesis of proteins are also added to the cell-free lysate. These include creatine phosphate, creatine phosphokinase, dithiothreitol, t-RNA, the twenty amino acids, spermidine, potassium acetate, magnesium acetate, magnesium chloride. It was also found that the concentration of $K^+$ and $Mg^{++}$ in the mixture is important. For extract from each type of cells, but also for a specific picornavirus the $Mg^{++}$ and $K^+$ concentrations should be optimized for maximal virus production. Further, when there is an increased amount of each of GTP, CTP and UTP, an increased amount of $Mg^{++}$ is needed. It has been found that the concentration of the $K^+$ in the form of KOAc should be in the range of about 50 mM to 200 mM, and the concentration of the $Mg^{++}$ in the form of Mg(OAc)2 and/or $MgCl_2$ should be in the range of about 1 mM to 4 mM in the synthesis medium. The mixture is adjusted to the final volume by a buffer, HEPES, pH 7.4. The amounts specified for the nucleoside triphosphates represents the final concentration in the mixture.

For the synthesis of polioviruses and rhinoviruses, a HeLa cell lysate is found to be particularly suitable. It was prepared as follows:

HeLa S3 cells ($5\times10^5$ cells/ml) were harvested by centrifugation, washed 3 times with phosphate buffer saline (PBS), and resuspended in 1.5 packed cell volume of 10 mM Hepes, pH 7.4 containing 10 mM KOAc, 1.5 mM Mg(OAc)2 and 2.5 mM dithiothreitol (DTT). Cells were left on ice for 10 min and disrupted at 4° C. with 15–25 strokes in a Dounce homogenizer. Nuclei were removed by centrifugation for 5 min at 2000 rpm and the mitochondrial fraction was removed from supernatant by centrifugation for 20 min at 10,000 rpm in SS34 rotor. The supernatant (S10 extract) was dialyzed for 2 hr against 100 vol 10 mM Hepes, pH 7.4, 90 mM KOAc, 1.5 mM Mg(OAc)2 and 2.5 mM DTT. The retained S10 extract was then centrifuged for 10 min at 10,000 rpm in SS34 rotor and the supernatant was stored at −80° C. On the next day, the S10 extract was thawed to room temperature, centrifuged in an Eppendorf centrifuge for 10 min at 10,000 rpm. The extract was treated with micrococcal nuclease (15 μg/ml extract) in the presence of $CaCl_2$ (7.5 μl of 0.1 M $CaCl_2$ /ml extract) at 20° C. for 15 min. The reaction was terminated by addition of 15 μl 1 20 mM EGTA/ml extract (S10 lysate). The S10 lysate was adjusted to 10% glycerol and stored for up to one month in small portions at −80° C. or, for longer term storage, at the temperature of liquid nitrogen.

The in vitro translation reaction mixture was prepared by mixing 93 μl S10 lysate with 1 mM ATP, 125 μM each of GTP, UTP and CTP, 10 mM creatine phosphate, 6 μg creatine phosphokinase, 2 mM DTT, 6 μg calf liver t-RNA, 12 μM each of 20 amino acid, 18 mM Hepes, pH 7.4, 240 μM spermidine, 0.1M KOAc, 0.35 mM $Mg(OAc)_2$, 0.75 mM $MgCl_2$ and 2 μg poliovirus RNA. The mixture was adjusted to 250 μl with distilled water. The K+ and Mg++ concentrations are in addition to those contributed from the S10 lysate, which was similar to that of the dialysis buffer.

It was found that the amount of GTP, CTP and UTP added can be varied from 20 μM to 1000 μM by adjusting the concentration of $Mg^{++}$. At lower concentrations of GTP, CTP and UTP the amount of $Mg^{++}$ can be reduced. At higher concentrations of GTP, CTP and UTP, an increased amount of $Mg^{++}$ is required. The amount of $Mg^{++}$ and $K^+$ should be adjusted for each type of cell extract or lysate, and for each type of picornavirus to be synthesized. Generally, the concentration of $K^+$ in the synthesis medium is from about 50 mM to 200 mM and the $Mg^{++}$ is from about 1 mM to 4 mM.

The synthesis of the infectious virus is programmed by adding the genomic RNA of the virus or in vitro synthesized viral RNA from cDNA to the cell-free medium. The viral RNA programmed cell-free medium is incubated from about 30° C. to 40° C. for a period of from about 2 to 24 hours.

The virus so formed can be quantitated and expanded from the cell-free medium by plaque assays and growth in the HeLa cells. The virus may be purified from the cell free medium by standard procedures.

To illustrate the effectiveness of the process, Poliovirus Serotype 1 (Mahoney), PVl(M) was used as a model. Other picornaviruses, such as rhinoviruses, aphthoviruses, cardioviruses may also be synthesized in like manner in appropriate cell free extracts. This is because picornaviruses have the same type of structures and the morphogenesis of the viruses are identical.

In the following examples, the successful in vitro synthesis de novo of PV1(M) in a cell-free extract is demonstrated.

EXAMPLE 1

Purification Of Poliovirus RNA

To an aliquot of the CsCl-purified poliovirus SDS (sodium deodecyl sulfate) was added to a final concentration of 0.1%. The suspension was vortexed for one minute after which an equal volume of phenol-chloroform (1:1 mixture) was added and the vortexing step was repeated. The mixture was centrifuged for 10 minutes at 4° C. in a microfuge at 14000 RPM. The aqueous phase was removed and the organic phase was washed with ½ volume of 10 mM Tris-HCl, pH 7.5, 1 mM EDTA. The aqueous phases were combined and extracted once more with phenol-chloroform and two times with chloroform. The RNA was precipitated from the aqueous phase by the addition of 2.5 volumes of ethanol and ammonium acetate to a final concentration of 1 M. The precipitate was resuspended in water and the RNA concentration was determined by measuring the optical density at 260 mμ.

EXAMPLE 2

Preparation of Cell-Free Extract

HeLa S3 cells ($5\times10^5$ cells/ml) were harvested by centrifugation, washed 3 times with phosphate buffered saline (PBS), and resuspended in 1.5 packed cell volume of 10 mM Hepes, pH 7.4 containing 10 mM KOAc, 1.5 mM $Mg(OAc)_2$ and 2.5 mM dithiothreitol (DTT). Cells were left on ice for 10 min and disrupted at 4° C. with 15–25 strokes in a Dounce homogenizer. Nuclei were removed by centrifugation for 5 min at 2000 rpm and the mitochondrial fraction was removed from supernatant by centrifugation for 20 min at 10,000 rpm in SS34 rotor. The supernatant (S10 extract) was dialyzed for 2 hr against 100 vol 10 mM Hepes, pH 7.4, 90 mM KOAc, 1.5 mM Mg(OAc)2 and 2.5 mM DTT. The retained S10 extract was then centrifuged for 10 min at 10,000 rpm in SS34 rotor and the supernatant were stored at −80° C. On the next day, the S10 extract was thawed to room temperature, centrifuged in an Eppendorf centrifuge for 10 min at 10,000 rpm. The supernatant was treated with micrococcal nuclease (15 μg/ml extract) in the presence of $CaCl_2$ (7.5 μl 0.1 M $CaCl_2$ ml extract) at 20° C. for 15 min. The reaction was terminated by addition of 15 μl 200 mM EGTA/ml S10 extract. The S10 lysate was adjusted to 10% glycerol and stored in small portions at −80° C. In vitro translation reaction mixtures (250 μl) contained 93 μl S10 lysate and the following additions: 1 mM ATP, 125 μM each of GTP, UTP, CTP, 10 mM creatine phosphate, 6 μg creatine phosphokinase, 2 mM DTT, 6 μg calf liver t-RNA, 12 μM each of 20 amino acid, 18 mM Hepes, pH 7.4, 240 μM spermidine, 0.1 M KOAc, 0.35 mM Mg(OAc)2, 0.4 mM $MgCl_2$ and 2 μg PV1(M) RNA. The final volume was made to 250 μl with distilled water. The mixture was incubated for 15 hours at 30° C.

The incubated mixture was analyzed by a plaque forming assay to determine the number of infectious virions formed. The amounts of each of GTP, CTP and UTP were varied in six experiments from 62.5 to 1000 μM. The results are presented in Table 1.

TABLE 1

Effect of Amount of NTP[a]

| NTPs (μM each) | Plaque No./ml |
|---|---|
| Control[b] | 595 |
| 62.5[c] | 3200 |
| 125[c] | 40,000 |
| 250[c] | 41,000 |
| 500[c] | 9590 |
| 1000[c] | 0 |

[a]all samples contained 1000 μM ATP.
[b]50 μM GTP added.
[c]each of CTP, UTP and GTP added.

Although the addition of 500 μM or 1000 μM of each of GTP, CTP and UTP appeared to reduce the amount of virus produced, it was found that production of virus was restored to a good level by adjusting the total $Mg^{++}$ concentration to 2.75 mM for 500 μM each of added NTPs and 3.00 mM for the 1000 μM each of added NTPs. This shows that the $Mg^{++}$ concentration should be adjusted for optimal production of virus.

For the purposes of studying the proteins formed in the in vitro synthesis, the amino acid methionine was replaced with $^{35}S$-methionine so that the proteins can be visualized by SDS gel analysis.

Figure 2:
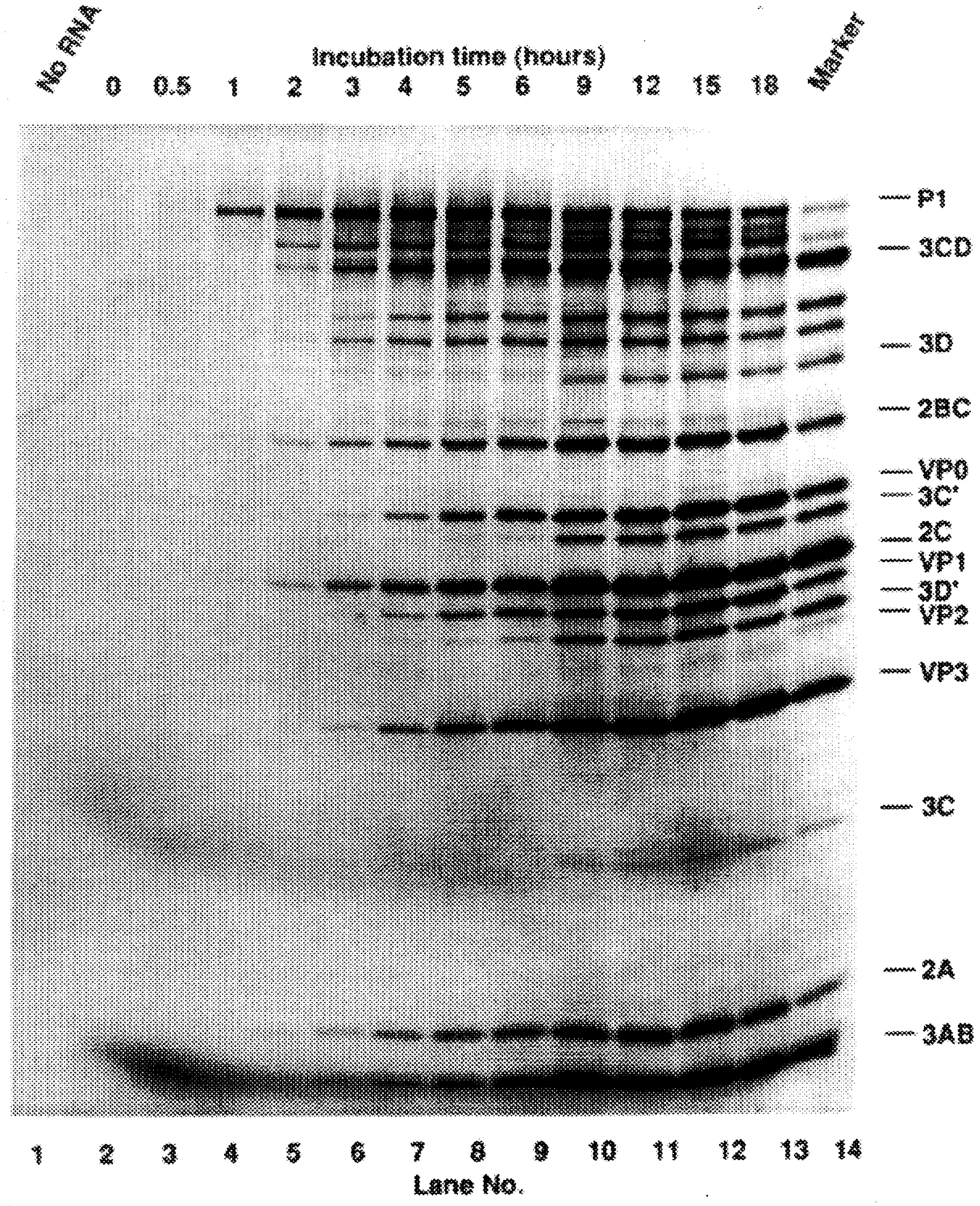
FIG. 2 is a photograph of SDS/polyacrylamide gel of the vital proteins formed in the in vitro synthesis of poliovirus over time. P1, 3CD, 3D, 2BC, VP0, 3C', 2C, VP1, 3D', VP2, VP3, 3C, 2A and 3AB shown on the right designate the various cleavage products and polyproteins of the poliovirus.

SDS gel analysis as shown in FIG. 2 shows the formation of VP0, VP1, VP2, VP3. VP2 was not immediately evident in FIG. 2, lane 13, although on longer exposure of the film, a band migrating to the position of VP2 emerged. VP4 being a very small protein is not retained on the gel. However, since VP4 and VP2 are cleavage products of VP0, the presence of VP2 shows that VP4 was formed.

When the concentration of $MgCl_2$ in the in vitro translation reaction mixture was increased from 0.4 to 0.75 mM, the yield of infectious virus produced was further increased by about 60%. And, when the total $Mg^{++}$ concentration was adjusted with increased µMs of NTPs added, the production of virus was maintained at the higher level. For example, when the total $Mg^{++}$ concentration was increased to 3.10 mM for 500 µM each of added NTPs and 3.35 mM for 1000 µM each of add NTPs, the production of infectious virus was increased.

EXAMPLE 3

Comparison of in vitro and in vivo Synthesized Virus

A plasmid pT7XL was constructed in accordance with the procedure described in Van Der Werf et al. (16) for pT7PV1-5. See FIG. 1. Plasmid pPV16 has the full length poliovirus cDNA, on an EcoRI fragment from pDS303, inserted in the counterclockwise orientation in the EcoRI site of pNT4.

To construct PT7 $PV_{1-5}$, the process used was as follows: An EcoRI-BamHI fragment containing the first 220 base pairs of poliovirus cDNA was isolated from pPV16 and digested with AluI. To this digest was added a synthetic DNA duplex that, upon ligation to the AluI-BamHI fragment, would reconstruct nucleotide 1-9 of the polio cDNA and place restriction sites for BamHI and NsiI immediately ahead of the polio sequence after ligation with T4 DNA ligase. The mixture was cut with BamHI, and the desired fragment was purified and cloned into the BamHI site of pBR322 to produce plasmid pJB126.

Plasmid pJB126 was cut at its unique NsiI site, and the resulting 3' extension was eliminated by digestion with Klenow fragment of *E coli* DNA polymerase to produce a blunt ended fragment beginning at the first nucleotide of polio DNA. The DNA extending from this site to the PvuI site was ligated to the large Pvu-StuI fragment of plasmid pAR2369 to create plasmid pJB127, in which the first nucleotide of the polio sequence is located two nucleotides past the RNA start site of the Ø10 promoter. The sequence for the segment containing the Ø10 promoter is shown in FIG. 1.

Plasmid pAR2369 is a derivative of PBR322 that contain the Ø10 promoter for T7 RNA polymerase. pAR2369 contains the Ø10 promoter in the BamHI site of pBR322, nucleotides −26 to +2 (SEQ ID NO:6) relative to the start site. A BamHI site lies immediately upstream of the promoter containing fragment, immediately downstream, the AGG (SEQ ID NO:7) at the RNA start site of Ø10 (−1 to +2) is half of a StuI site (AGGCCT) (SEQ ID NO:3), which is followed immediately by a BamHI site in the sequence AGGCCTGGATCC (SEQ ID NO:4). This is the only StuI site in the plasmid. StuI cuts at the center of its recognition sequence, leaving a blunt end AGG (SEQ ID NO:7) at position −1 to +2. The fragment inserted at this site would produce RNAs having only an additional pair of GG (SEQ ID NO:8) at their 5' end.

The complete polio DNA sequence was reconstituted from pPV16 and pJB127 by taking advantage of the cutting specificity of BglI, which cuts after the seventh nucleotide in the sequence GCCNNNNNGGC (SEQ ID NO:5). Five different fragments: A, B from pPV16 and D, F, G, from pJB127 must be ligated to reconstitute the desired plasmid PT7 $PV_{1-5}$. This was done simply by ligating the mixture of five fragments (FIG. 1) which will uniquely assemble in the correct orientation. Restriction analysis and limited DNA sequencing verified that the desired plasmid, designated PT7 $PV_{1-5}$ was obtained. In this plasmid, the cDNA of PV1(M) was placed under the control of a promoter for T7 RNA polymerase. The transcription product is mRNA of PV1(M).

The reaction mixture contained 20 µg/ml of Eco RI-cut pT7XL DNA, 400 µM ribonucleoside triphosphates, 8 mM $MgCl_2$, 4 mM spermidine, 25 mM potassium phosphate buffer pH 7.5, 10 mM dithiothreitol and 15 µg of T7 RNA polymerase per ml. After incubation for 30 minutes at 37° C., 10 µl of 0.5 M EDTA were added. The RNA was extracted by phenol-chloroform and precipitated by the addition of 3 volumes of ethanol with ammonium acetate at a final concentration of 1M.

Translation reactions were same as those described in Example 2 and 2 µl of 1 mM cold methionine and 300 ng each of pT7XL or PV1(M) RNA were incubated in a total volume of 37.5 µl. Incubation was for 15 hr at 30° C. The samples were then treated with RNAse A (20 µg/ml) and RNAse T1 (100 U/ml) for 30 min at room temperature. A plaque assay as described in Example 4 was conducted. The results showed that the viruses formed under the direction of both viral RNA and in vitro transcribed RNA were identical to that derived from in vivo grown viruses.

EXAMPLE 4

Plaque Forming Assay

Full length, plus-stranded poliovirus RNA is infectious when added to tissue culture cells, but the specific infectivity is low (10 infectious centers per µg of purified RNA; see Koch (15). The efficiency of transfection can be increased by a factor of $10^5$, if the host cells are pre-treated with polycations. In view of these properties of viral RNA, the formation of plaques observed here could be the result of transfection of monolayer cells with the RNA used for translation. To test this possibility, we assayed for plaque forming units (PFU) in the complete incubation mixture (cell extract, translation mixture, plus template RNA) (i) before translation, and (ii) after 15 hr. of translation, but only after the mixtures had been treated with RNase A and RNase T1 prior to the addition to cells.

A lawn of HeLa cells (HeLa cell monolayer) was prepared in petri dishes. Each of the incubation mixture to be tested was diluted to 200 µl with PBS and separately placed on each monolayer. The following procedure was used. Six well plates of confluent HeLa R19 cells were washed with phosphate buffered saline. A dilution of the virus (200 µl ) were added per well and the plates were rocked gently for 30 min. To each well 2 ml of overlay medium was added which was made up of 22.5 ml of 2X MEM, 25 ml of 2% noble agar and 2.5 ml of calf serum. The plates were incubated at 37° C. for 48 hours and the cells were stained with crystal violet (1% crystal violet in 50% methanol).

Figure 3:
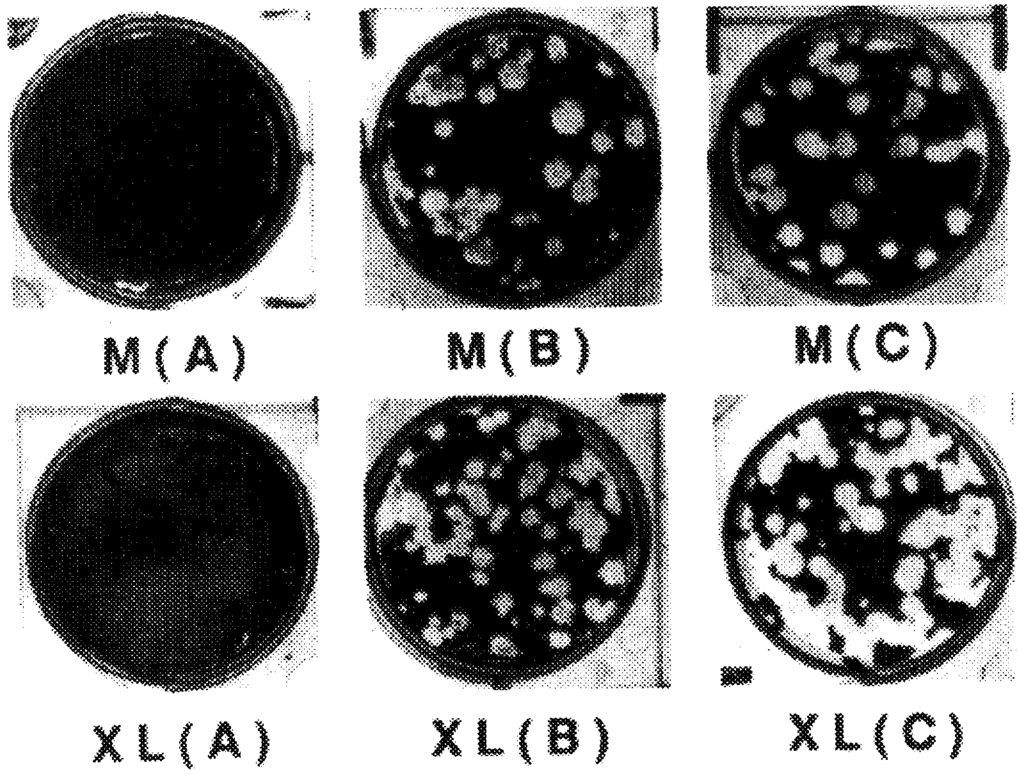
FIG. 3 is a photograph of the plaque-forming test results using RNA transcribed from plasmid PT7 PV1-5: XL(A) and XL(B), compared with viral RNA: M(A) and M(B). XL(C) and M(C) are plaque formed by native virus for comparison. M(A) shows the results for viral RNA incubated for 15 hours in cell lysate alone and M(B) shows the results for viral RNA incubated for 15 hours in the cell-free medium of the present invention. Whereas, XL(A) and XL (B) show the formation of plaques after plasmid PT7 $PV_{1-5}$ was incubated for 15 hours respectively in cell lysate and in the cell-free medium of the present invention.

The experiments were carried out either with RNA derived by in vitro transcription of plasmids containing full-length poliovirus cDNA or with virion RNA of PV1(M). No plaques were generated from the zero-time incubation mixture (see Example 6), but they reproducibly formed from the 15 hr. incubation mixture in spite of RNase treatment. See FIG. 3. The following observation suggested that in vitro translation was required for the formation of PFUs: no plaques were observed if the viral RNAs were incubated for 15 hr. with the cell lysate alone (without addition of the translation mixture, e.g., ATP, GTP, tRNA, amino acids, etc.) Plaques resulting from in vitro translation mixtures [XL(B) and M(B)] were compared with those obtained from in vivo grown virus [XL(C) and M(C)]. No difference in plaque morphology is apparent.

EXAMPLE 5

Confirmation By PCR

The replication of the poliovirus genome proceeds through the synthesis of plus- and minus-stranded RNAs. Virion RNA is, by definition, plus-stranded RNA because it is of messenger-sense polarity. Both virion and transcription-derived RNAs used in translations are therefore plus strands. Since poliovirions are thought not to contain minus strands, the detection of such strands in the incubation mixture programmed with virion RNA would be indicative of virus-specific RNA synthesis. Therefore, we have tested the incubation mixture for poliovirus-specific minus strands by cDNA synthesis and amplification with the polymerase chain reaction (PCR).

Translation reactions were same as those described in Example 1. After 15 hr incubation, the RNAs were extracted by standard method and resuspended in 20 μl of water. Generally, 5 μl samples were used for cDNA synthesis. The following oligonucleotides were used for the synthesis of cDNA and PCR primer pairs.

Primer 1 (SEQ ID NO 1)

PV1(M) [plus] (3280–3301) 5' AGTCTGGTGC-CCGCGTCCACCG 3'

Primer 2 (SEQ ID NO 2)

PV1(M) [minus] (3983–4007) 3' CCTGAGTGGC-CAAGTGGTAGTTGC 5'

Primer 1 chosen for cDNA synthesis was of plus strand polarity, primer 2, used for amplification (together with primer 1), was of minus strand polarity. The DNA product to be expected from such reaction is 178 nucleotides long. cDNA transcripts were prepared by incubation (42° C., 2 hr) of RNA templates in 50 μl reaction mixtures containing 50 mM Tris-HCl, pH 8.3, 70 mM KCl, 5 mM $MgCl_2$, 10 mM DTT, PCR primers (50 pmoles), 200 μM each of dATP, dCTP, dGTP, dTTP, 25 U RNasin, and 40 U avian myeloblastosis virus (AMV) reverse transcriptase. Reactions were terminated by addition of 2 μl 0.5M EDTA, pH 8.0, followed by 5 μl of 750 mM NaOH.

Figure 4:
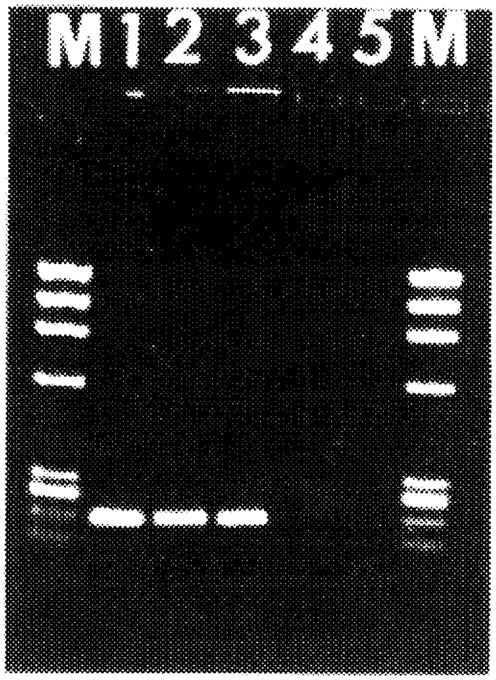
FIG. 4 is a photograph of the gel electrophoresis results obtained in the PCR reaction. Lanes M are molecular weight markers.

The samples were incubated at 65° C. for 1 hr and were neutralized by the addition of 12.5 μl 2M Tris-HCl, pH 8.0 and 5 μl 5M HCl. The samples were extracted with phenol/chloroform and cDNA was separated from unincorporated dNTPs by gel filtration using push column, precipitated with ethanol, dried and dissolved in 20 μl water. Five μl cDNA products were diluted to 100 μl reaction mixtures containing PCR primers (50 pmoles each) and 2.5 U of thermostable DNA polymerase from Thermus aquaticus (Taq DNA polymerase) and overlaid with mineral oil. Programmed amplification cycles (denaturation: 94, 1 min; annealing: 60° C., 30 sec.; extension: 72° C., 45 sec.) were performed by a DNA thermal cycler (Perkin Elmer-Cetus). Samples of the amplification reactions were loaded into 0.8% agarose gel containing 5 μg/ml ethidium bromide, and the fluorescent DNA bands were visualized on a transilluminator. The results are shown in FIG. 4. In FIG. 4, lane 1, this fragment was generated simply from a PCR reaction using poliovirus infectious cDNA as template. As can be seen in FIG. 4, lane 2, a band of the same chain length was generated from total RNA isolated after 15 hr of translation but no band was seen at 0 hr of incubation (lane 4). The latter is a control confirming that virion RNA used in this translation does not contain minus strands (note that we were unable to use plasmid-derived RNA for this experiment because we found it difficult to remove all plasmid DNA prior to PCR). Similarly, no band was seen when the reaction was carried out with total RNA of the HeLa extract to which no viral RNA had been added but the translation mixture had been omitted (lane 5). A band of the expected size was also found when virion RNA was used as template for cDNA synthesis, but this required priming with the minus strand primer 2 (lane 3). These data clearly show the presence of poliovirus-specific minus strands synthesized after translation of viral RNA in vitro; thus, the reaction mixture must have generated active poliovirus RNA polymerase.

EXAMPLE 6

Incubation Time For Synthesis

A time course study of the in vitro synthesis process was conducted using the procedure as described in Example 1. The results show:

TABLE 2

| Time (hours) | PFU/ml |
|---|---|
| 0 | 0 |
| 5 | 0 |
| 10 | 400 |
| 15 | 41,000 |
| 20 | 40,000 |

EXAMPLE 7

Effect Of Guanidine HCl On In Vitro Synthesis Of PV1(M)

Guanidine hydrochloride (Gua HCl) is a compound known to strongly inhibit poliovirus RNA replication in HeLa cell at a concentration of 2 mM. At this concentration, the drug has no adverse effect on the metabolism and growth of HeLa cells themselves for several cell divisions. Poliovirus variants resistant to 2 mM Gua HCl can be readily selected; their mutation(s) map to a specific locus in the non-structural polypeptide 2C, a locus highly conserved amongst 2C polypeptides of all picornaviruses. The involvement of 2C in RNA replication has been demonstrated recently also by analyses of 2C mutants generated by site-directed mutagenesis.

The results are presented in Table 3 below. Without Gua HCl in the incubation mixture, the translation of RNA derived from wild-type poliovirus which is guanidine sensitive, PV1(M)$g^s$, lead to the formation of infectious virus. On the other hand, the presence of 2 mM Gua HCl in the incubation mixture prevented completely the formation of PFUs (Table 3). In contrast, when RNA from a guanidine-resistant poliovirus PV1(M)$g^r$, was used as template for translation, infectious virus was produced (Table 3) whether Gua HCl was added.

EXAMPLE 8

Effect of Antibodies On In Vitro Synthesis Of PV1M

Poliovirus occurs in three distinct serotypes that share the same receptor on HeLa cells. Treatment of the monolayer HeLa cells with monoclonal antibodies D171, which completely blocks the uptake of poliovirus into host cells, prior to addition of the incubation mixture completely inhibited plaque formation (Table 3). Similarly, no plaques were observed when the incubation mixture was treated with anti-PV1(M) rabbit hyperimmune serum (Table 3). Neutralization of the in vitro synthesized virus was type specific: the RNA used for translation is specific for type 1 (Mahoney); accordingly, anti-poliovirus type 3 (Leon), PV3(L), hyperimmune serum did not reduce the titer in the cell-free extract (Table 3). The results suggest that intact poliovirions of serotype 1 (Mahoney) were synthesized in the cell-free extract, and that on subsequent incubation of HeLa cells, these virions entered the cells by a poliovirus receptor-mediated pathway.

TABLE 3

Effect Of Antibodies And Inhibitors On The Synthesis Of Poliovirus In The Incubation Mixture[a].

| | PFU/ml | | | | | | | | | | | |
|---|---|---|---|---|---|---|---|---|---|---|---|---|
| | Gua-HCl | | Anti-receptor mcAB D171 | | Anti-PV1(M) Ab | | Anti-PV3(L) Ab | | $Mg^{++b}$ | | edeine | |
| RNA | – | +[c] | – | + | – | + | – | + | – | +[d] | – | +[e] |
| PV1(M)g[a] | 24,948 | 0 | 24,965 | 0 | 21,868 | 0 | 15,932 | 15,924 | 0 | 12,000 | 12,000 | 0 |
| PV1(M)g[r] | 400 | 2,220 | ND[f] | ND | ND | ND | ND | ND | ND | ND | ND | ND |

a) conditions were exactly same as in Table 2 but with different batches of HeLa S10 lysate.
b) no addition of extra $Mg^{++}$ and NTPs but the lysate contained 1.5 mM of $Mg^{++}$.
c) with 2.0 mM guanidine HCl.
d) with additional 1.10 mM $Mg^{++}$.
e) with 4 μM edeine.
f) ND, not determined.

After treatment with RNAses, the samples were diluted to 200 μl in the presence of 1 μg/ml of anti PV1(M) (D171) monoclonal antibody (Ab) or 25 μl each of PV1(M) or PV1(L) hyperimmunesera, preincubated at room temperature for 20 min and then plaque assays were performed as described in Example 4.

Based on the results obtained, it is clear that infectious poliovirus type 1 (Mahoney) was synthesized de novo in an in vitro process. The product was as infectious as the natural virus. Moreover, the specific tests by guanidine HCl and antibodies specific to PV1(M) shows that the virus synthesized is the PV1(M).

EXAMPLE 9

Preparation of Rhinovirus 14

Following the procedure of Example 1, the RNA of Rhinovirus 14 (HRV-14) was obtained. Following the procedure of Example 2, the RNA of the HRV-14 was incubated at a temperature of 30° C. in a translation mixture of a cell-free extract of HeLa S3 cells except that 90 mM KOAC, 0.35 mM $Mg(OAC)_2$ and 0.4–0.5 mM $MgCl_2$ was added to the mixture.

After the mixture was incubated for 10–15 hrs., ribonuclease was added to destroy the naked, non-encapsidated viral RNA. The mixture was then added to a monolayer of HeLa cells. The monolayer of HeLa cells was incubated at 35° C. 10–40 plaque forming units, detected as defined areas of destroyed HeLa cells, were observed.

Although there are over 100 serotypes of human rhinoviruses, the biology and molecular biology of these viruses are very similar. It is expected that the procedure for synthesizing in vitro rhinovirus-14 will be applicable to all of the rhinoviruses.

Although the invention was illustrated by the use of specific examples, the examples were provided to illustrate the invention and is not to be used to limit the scope of the invention.

We claim:

1. A process for the de novo, in vitro synthesis of picornaviruses comprising:

A. Preparing a lysate from transformed or tumorigenic mammalian cells selected from the group consisting of kidney cells, epithelial cells, liver cells, cells of the central nervous system, and fibroblastic cells, by removing nuclei and mitochondria from the cells to form an extract, and then deactivating mRNA endogenous to the cells in the extract with micrococcal nuclease, calcium chloride and EGTA;

B. Preparing an in vitro synthesis medium by mixing:
(i) said lysate,
(ii) about 1 mM ATP,
(iii) about 20 μM to 1000 μM each of GTP, CTP and UTP, or 50 μM of GTP,
(iv) about 10 mM creatine phosphate,
(v) about 24 μg/ml creatine phosphokinase,
(vi) about 2 mM dithiothreitol,
(vii) about 24 μg/ml calf liver t-RNA,
(viii) about 12 μM each of 20 amino acids,
(ix) about 18 mM Hepes, pH 7.4,
(x) about 240 μM spermidine,
(xi) about 50 mM to 200 mM potassium acetate, and
(xii) from about 0.75 mM to 4 mM $Mg^{++}$,
wherein the amounts specified represent the final concentration in the medium;

C. Adding picornavirus RNA or in vitro synthesized RNA from picornavirus cDNA to the in vitro synthesis medium; and D. Incubating the in vitro synthesis medium resulting from step C for from about 4 to 24 hours at a temperature of from about 30° C. to 40° C. to produce a mixture of fully assembled virions in the presence of the in vitro synthesis medium, viral RNA, synthesized viral protein and partially assembled virious.

2. A process according to claim 1, further comprising freezing the extract at −80° C., thawing to room temperature and centrifuging before deactivating the endogenous mRNA.

3. A process according to claim 2, wherein the concentration of each of GTP, CTP and UTP is in the range of about 40 μM to 250 μM.

4. A process according to claims 1, 2 or 3, wherein the in vitro synthesis medium resulting from step C is incubated about 10 to 20 hours.

5. A process according to claim 1, wherein the incubating temperature is about 34° C.

6. A process for the de novo, in vitro synthesis of polioviruses comprising:

A. Preparing a lysate from transformed or tumorigenic mammalian cells selected from the group consisting of kidney cells, epithelial cells, liver cells, cells of the central nervous system, and fibroblastic cells, by removing nuclei and mitochondria from the cells to form an extract, and then deactivating mRNA endogenous to the cells in the extract with micrococcal nuclease, calcium chloride and EGTA;

B. Preparing an in vitro synthesis medium by mixing:
(i) said lysate,
(ii) about 1 mM ATP,
(iii) about 20 μM to 1000 μM each of GTP, CTP and UTP, or 50 μM of GTP,
(iv) about 10 mM creatine phosphate,
(v) about 24 μg/ml creatine phosphokinase,
(vi) about 2 mM dithiothreitol,
(vii) about 24 μg/ml calf liver t-RNA,
(viii) about 12 μM each of 20 amino acids,
(ix) about 18 mM Hepes, pH 7.4,
(x) about 240 μM spermidine,
(xi) about 50 mM to 200 mM potassium acetate, and
(xii) about 0.75 mM to 4 mM $Mg^{++}$,
wherein the amounts specified represent the final concentration in the medium;

C. Adding poliovirus RNA or in vitro synthesized RNA from poliovirus cDNA to the in vitro synthesis medium; and D. Incubating the in vitro synthesis medium resulting from step C for about 4 to 24 hours at a temperature of from about 30° C. to 40° C. to produce a mixture of fully assembled virions in the presence of the in vitro synthesis medium, viral RNA, synthesized viral protein and partially assembled virions.

7. A process according to claim 6, further comprising freezing the extract at −80° C., thawing to room temperature and centrifuging before deactivating the endogenous mRNA.

8. A process according to claim 7, wherein the mammalian cells are HeLa cells.

9. A process according to claim 8, wherein the concentration of each of GTP, CTP and UTP is in the range of about 40 μM to 250 μM.

10. A process according to claims 7, 8, or 9, wherein the in vitro synthesis medium resulting from step C is incubated about 10 to 20 hours.

11. A process according to claim 9, wherein the incubating temperature is about 34° C.

12. A process for the de novo, in vitro synthesis of rhinoviruses comprising:

A. Preparing a lysate from transformed or tumorigenic mammalian cells selected from the group consisting of kidney cells, epithelial cells, liver cells, cells of the central nervous system, and fibroblastic cells, by removing nuclei and mitochondria from the cells to form an extract, and then deactivating mRNA endogenous to the cells in the extract with micrococcal nuclease, calcium chloride and EGTA;

B. Preparing an in vitro synthesis medium by mixing:
  (i) said lysate,
  (ii) about 1 mMATP,
  (iii) about 20 μM to 1000 μM each of GTP,
CTP and UTP, or 50 μM of GTP,
  (iv) about 10 mM creatine phosphate,
  (v) about 24 μg/ml creatine phosphokinase,
  (vi) about 2 mM dithiothreitol,
  (vii) about 24 μg/ml calf liver t-RNA,
  (viii) about 12 μM each of 20 amino acids,
  (ix) about 18 mM Hepes, pH 7.4,
  (x) about 240 μM spermidine,
  (xi) about 50 mM to 200 mM potassium acetate, and
  (xii) about 0.75 mM to 4 mM $Mg^{++}$,
wherein the amounts specified represent the final concentration in the medium;

C. Adding rhinovirus RNA or in vitro synthesized RNA from rhinovirus cDNA to the in vitro synthesis medium; and D. Incubating the in vitro synthesis medium resulting from step C for about 4 to 24 hours at a temperature of about 30° C. to 40° C. to produce a mixture of fully assembled virions in the presence of the in vitro synthesis medium, viral RNA, synthesized viral protein and partially assembled virions.

13. A process according to claim 12, further comprising freezing the extract at −80 ° C., thawing to room temperature and centrifuging before deactivating the endogenous mRNA.

14. A process according to claim 13, wherein the mammalian cells are HeLa cells.

15. A process according to claim 14, wherein the concentration of each of GTP, CTP and UTP is in the range of about 40 μM to 250 μM.

16. A process according to claims 13, 14 or 15, wherein the in vitro synthesis medium resulting from step C is incubated about 10 to 20 hours.

17. A process according to claim 15, wherein the incubating temperature is about 37° C.

18. A process according to claim 1, wherein the picornavirus is Encephalomyocarditis virus.

* * * * *